(12) United States Patent
Russak

(10) Patent No.: US 9,988,675 B2
(45) Date of Patent: *Jun. 5, 2018

(54) RATE BASED IDENTIFICATION OF REACTION POINTS

(75) Inventor: Ze'ev Russak, Ramat Gan (IL)

(73) Assignee: AZURE VAULT LTD., Ramat-Gan (IL)

( * ) Notice: Subject to any disclaimer, the term of this patent is extended or adjusted under 35 U.S.C. 154(b) by 0 days. days.

This patent is subject to a terminal disclaimer.

(21) Appl. No.: 13/985,314

(22) PCT Filed: Mar. 13, 2012

(86) PCT No.: PCT/IB2012/051182

§ 371 (c)(1),
(2), (4) Date: Aug. 14, 2013

(87) PCT Pub. No.: WO2012/123895

PCT Pub. Date: Sep. 20, 2012

(65) Prior Publication Data

US 2013/0323743 A1 Dec. 5, 2013

Related U.S. Application Data

(60) Provisional application No. 61/453,108, filed on Mar. 15, 2011.

(51) Int. Cl.
 *C12Q 1/68* (2018.01)
 *G06F 17/30* (2006.01)
 *G06F 19/00* (2018.01)

(52) U.S. Cl.
 CPC ........... *C12Q 1/686* (2013.01); *G06F 19/702* (2013.01)

(58) Field of Classification Search
 CPC ........ G06F 19/18; G06F 19/70; G06F 19/702; G06F 19/708; G06F 19/707
 See application file for complete search history.

(56) References Cited

U.S. PATENT DOCUMENTS

| | | | |
|---|---|---|---|
| 6,503,720 B2 | 1/2003 | Wittwer et al. | |
| 6,783,934 B1 | 8/2004 | McMillan et al. | |
| 6,911,327 B2 | 6/2005 | McMillan et al. | |
| 7,680,604 B2 * | 3/2010 | Kurnik | 702/19 |
| 7,680,868 B2 * | 3/2010 | Kurnik et al. | 708/270 |
| 7,991,562 B2 * | 8/2011 | Kurnik et al. | 702/19 |
| 2003/0194122 A1 | 10/2003 | Stone et al. | |
| 2006/0224330 A1 | 10/2006 | Kurnik et al. | |
| 2007/0073490 A1 | 3/2007 | Kurnik et al. | |
| 2007/0124088 A1 | 5/2007 | Woo et al. | |
| 2007/0129899 A1 | 6/2007 | Ward et al. | |
| 2007/0148632 A1 | 6/2007 | Kurnik et al. | |
| 2009/0119020 A1 | 5/2009 | Kurnik et al. | |
| 2010/0070190 A1 | 3/2010 | Lerner | |

FOREIGN PATENT DOCUMENTS

WO 03029924 A2 4/2003

OTHER PUBLICATIONS

"OriginLab® Origin: Fitting Multiple Peaks with Peak Analyzer", http://youtu.be/FrpU662NAkl, uploaded Jul. 28, 2009.*
International Search Report and Written Opinion dated Jul. 19, 2012 in corresponding International Application No. PCT/IB2012/051182.
Brechtbuehl et al., A rapid real-time quantitative polymerase chain reaction for hepatitis B virus. J Virol Methods. Apr. 2001;93(1-2):105-113.
Lee et al., ResonSense: simple linear fluorescent probes for quantitative homogenous rapid polymerase chain reaction. Analytica Chimica Acta 2002,;457:61-70.
Palais and Wittwer, Mathematical Algorithms for High-Resolution DNA Melting Analysis. Methods Enzymol. 2009;454:323-343.

* cited by examiner

*Primary Examiner* — Michael Borin
(74) *Attorney, Agent, or Firm* — Acuity Law Group, P.C.; Michael A. Whittaker

(57) ABSTRACT

An apparatus for identifying transition points in a chemical reaction, the apparatus comprising: a property value receiver, configured to receive a plurality of values of a physical property of the chemical reaction, a function calculator, associated with the property value receiver, configured to calculate a function and verify that the function has a line of best fit with a same slope as a linear function connecting two of the received values, the two values pertaining to a start and end of a time period, a difference calculator, associated with the function calculator, configured to calculate a difference between the calculated function and a plurality of the received values pertaining to the time period having the start and end, and a transition point identifier, associated with the difference calculator, configured to identify at least one transition point of the chemical reaction, using the calculated difference.

26 Claims, 10 Drawing Sheets

RATE BASED IDENTIFICATION OF REACTION POINTS

FIELD AND BACKGROUND OF THE INVENTION

The present invention relates to analyzing, monitoring and controlling chemical reactions and, more particularly, but not exclusively to systems and method for identifying specific points in chemical reactions, such as a point in a chemical reaction, in which a new stage of the chemical reaction begins.

Chemical reaction may need to be characterized in real-time.

For example, detection and quantification of a molecule in a chemical reaction may be required to take place as the reaction progresses, in order to characterise the pattern of the reaction, take certain steps when the reaction moves into a new phase, etc.

Of special interest are a point of start of exponential growth of the chemical reaction product and a point where growth of the product begins to slow to a halt, also referred to as elbow points. The elbow points may be used to determine whether any reaction products have been produced. The magnitude of the reaction may be determined using a measured physical property of the reaction, say photometric measurements between the elbow points, as described in further detail hereinbelow.

One widely used and well-established laboratory technique is Polymerase Chain Reaction (PCR).

In PCR, the polymerase enzyme attaches to a target DNA sequence and replicates it exactly along with its containing chromosome or DNA strand. If the target DNA sequence is not present or for some reason is unavailable for attachment to the PCR enzyme, no replication of DNA takes place. This procedure is repeated many times in a PCR reaction instrument. Thus, the target DNA sequence, as well as overall DNA concentration, is amplified to microgram levels to allow for accurate detection and data analysis.

Quantitative Fluorescent Polymerase Chain Reaction (QF-PCR) is a widely used PCR method. QF-PCR is commonly used for diagnosis and research in fields such as disease (infectious or inherited), blood screenings, histology, oncology, tissue typing and drug discovery.

In QF-PCR, phosphate groups are introduced into the PCR reaction in order to mark the replicated molecules for purposes of real-time detection and quantification.

The two common methods for QF-PCR are: 1) Fluorescent dyes that intercalate with double-stranded DNA and 2) Modified DNA probes that fluoresce only when hybridised with the target DNA sequence, as known in the art.

The latter method is more sensitive and therefore more reliable and accurate, it also allows for real-time quantification of multiple DNA sequences using differently coloured probes.

The data received is in the form of fluorescent intensity, called FI.

The FI data may be represented using a graph. The shape of the graph may be either linear (if a target DNA sequence was not found or not amplified) or appear to be a sigmoid curve (if the target sequence DNA was amplified).

In case of presence of the target DNA sequence, there arises a need to identify the point where amplification of the DNA sequence begins to take place, also referred to as the threshold point or $C_T$. However, the FI data in the threshold's region usually has a low Signal to Noise Ratio (SNR). Consequently, determining $C_T$ with a high degree of accuracy requires a method or a combination of methods for refining the FI data.

In photometric methods such as QF-PCR, photometry is utilised for real-time detection and quantification of a reaction product.

In order to determine whether a) any reaction products have been produced, and b) the magnitude of production, targeted photoactive probes are utilised in the chemical reaction, to produce a photometric effect (i.e. light) detectable by an optical sensor. The magnitude of the production is derived from data pertaining to the intensity of the photometric effect.

Determining whether any reaction products have been produced, and the magnitude the production accurately is limited by the amount of noise in the recorded photometric data. The noise may originate from chemical sources, such as the reaction mix, as well as from electronic sources, such as the instrument used for light detection.

Several traditional methods have been used to determine time points of exponential growth on a graph representing a quantitative measurement of a chemical reaction over time.

One traditional method involves an n-derivative of light intensity used to determine time periods of exponential growth.

International Patent Application No.: PCT/US2002/031144, to Taylor et al., published on Apr. 10, 2003, entitled "Adaptive baseline algorithm for quantitative", describes baseline subtraction algorithms developed to reduce tube-to-tube and cycle-to-cycle variabilities during real time PCR amplification. Particularly, Taylor describes an algorithm for determining a threshold cycle, for detection of an amplified nucleic acid production.

U.S. patent application Ser. No. 11/645,964, to Woo et al., filed on Dec. 27, 2006, entitled "Automatic threshold setting and baseline determination for real-time PCR", discloses a method which involves a base-lining operation, for identifying the bounds of a baseline region and performing a linear interpolation to identify the characteristic equation defining the baseline.

U.S. patent application Ser. No. 11/316,315, to Kurnik et al., filed on Dec. 20, 2005, describes Systems and methods for determining characteristic transition values such as elbow values in sigmoid or growth-type curves, utilizing a Levenberg-Marquardt (LM) regression process.

U.S. patent application Ser. No. 11/861,188, to Kurnik et al., filed on Sep. 25, 2007, entitled "PCR elbow determination using curvature analysis of a double sigmoid", describes a method utilizing a first or second degree polynomial curve that fits the a growth type curve, and determination of a statistical significance value for the curve fit. The significance value indicates whether the data represents significant or valid growth.

Some traditional methods based on linear regression, are used to determine the time point where growth in light intensity changes from linear to exponential. Typically, the linear regression based methods include prior setting of a threshold for intensity, to determine the start of exponential growth.

A particular method involving two-phase regression is described in an article by Edna Schechtman, published in the Journal of Statistical Computation and Simulation, volume 17, issue 3, 1983 (pages 223-229), entitled "Inference in Two-Phase Regression: A Simulation study with Non-normal Observation".

Some currently used methods involve converting data into a graph image and rotating the image.

In a one example, U.S. patent application Ser. No. 11/349,538, to Kurnik, filed on Feb. 6, 2006, entitled "PCR elbow determination by rotational transform after zero slope alignment", describes PCR data set visualization in a two-dimensional plot of fluorescence intensity vs. cycle number. Then, the PCR data set is adjusted to have a zero slope.

In a second example, Japanese Patent Publication No. 2007128483, to Kurnik, published on May 24, 2007, entitled "PCR elbow determination by rotational transform", describes a rotation transform application to a modified data set, to rotate the data about a defined coordinate such as the origin, so that the data point representing the Ct value may become a minimum or a maximum along the intensity axis. The data point representing the elbow or Ct value of the curve is identified, and this data point is then reversed back and the cycle number of the data point is displayed.

U.S. patent application Ser. No. 11/423,377, to Kurnik, filed on Jun. 9, 2006, entitled "CT determination by cluster analysis with variable cluster endpoint", describes PCR data set visualized in a two-dimensional plot of fluorescence intensity (y-axis) vs. cycle number (x-axis). Then, the points of the plot are clustered. Using the identified clusters, a linear slope of each of the clusters is determined and the data point representing the elbow or Ct value of the PCR curve is identified as an end point of one of the identified clusters.

Other Methods, such as the one disclosed by Wittwer et al., in U.S. Pat. No. 6,503,720, combine two or more of the methods described hereinabove.

SUMMARY OF THE INVENTION

According to one aspect of the present invention there is provided an apparatus for identifying transition points in a chemical reaction, the apparatus comprising: a property value receiver, configured to receive a plurality of values of a physical property of the chemical reaction, a function calculator, associated with the property value receiver, configured to calculate a function and to verify that the function has a line of best fit with a same slope as a linear function connecting two of the received values, the two values pertaining to a start and end of a time period, a difference calculator, associated with the function calculator, configured to calculate a difference between the calculated function and a plurality of the received values pertaining to the time period having the start and end, and a transition point identifier, associated with the difference calculator, configured to identify at least one transition point of the chemical reaction, using the calculated difference.

According to a second aspect of the present invention there is provided a computer implemented method for identifying transition points in a chemical reaction, the method comprising steps the computer is programmed to perform, the steps comprising: a) receiving a plurality of values of a physical property of the chemical reaction, b) calculating a function and verifying that the function has a line of best fit with a same slope as a linear function connecting two of the received values, the two values pertaining to a start and end of a time period, c) calculating a difference between the calculated function and a plurality of the received values pertaining to the time period having the start and end, and d) identifying at least one transition point of the chemical reaction, using the calculated difference.

According to a third aspect of the present invention there is provided a computer readable medium storing computer executable instructions for performing steps of identifying transition points in a chemical reaction, the steps comprising: a) receiving a plurality of values of a physical property of the chemical reaction, b) calculating a function and verifying that the function has a line of best fit with a same slope as a linear function connecting two of the received values, the two values pertaining to a start and end of a time period, c) calculating a difference between the calculated function and a plurality of the received values pertaining to the time period having the start and end, and d) identifying at least one transition point of the chemical reaction, using the calculated difference.

According to a fourth aspect of the present invention there is provided a system for identifying transition points in a chemical reaction, the apparatus comprising: a chemical reaction apparatus, comprising at least one sensor configured to measure a plurality of values of a physical property of a chemical reaction, a property value receiver, associated with the chemical reaction apparatus, configured to receive the plurality of values of the physical property of the chemical reaction, a function calculator, associated with the property value receiver, configured to calculate a function and to verify that the function has a line of best fit with a same slope as a linear function connecting two of the received values, the two values pertaining to a start and end of a time period, a difference calculator, associated with the function calculator, configured to calculate a difference between the calculated function and a plurality of the received values pertaining to the time period having the start and end, and a transition point identifier, associated with the difference calculator, configured to identify at least one transition point of the chemical reaction, using the calculated difference.

According to a fifth aspect of the present invention there is provided an apparatus for identifying transition points in a chemical reaction, the apparatus comprising: a property value receiver, configured to receive a plurality of values of a physical property of the chemical reaction, a function calculator, associated with the property value receiver, configured to calculate a function having a line of best fit with a same slope as a linear function connecting two of the received values, the two values pertaining to a start and end of a time period, a difference calculator, associated with the function calculator, configured to calculate a difference between the calculated function and a plurality of the received values pertaining to the time period having the start and end, and a transition point identifier, associated with the difference calculator, configured to identify at least one transition point of the chemical reaction, using the calculated difference.

According to a sixth aspect of the present invention there is provided a computer implemented method for identifying transition points in a chemical reaction, the method comprising steps the computer is programmed to perform, the steps comprising: a) receiving a plurality of values of a physical property of the chemical reaction, b) calculating a function having a line of best fit with a same slope as a linear function connecting two of the received values, the two values pertaining to a start and end of a time period, c) calculating a difference between the calculated function and a plurality of the received values pertaining to the time period having the start and end, and d) identifying at least one transition point of the chemical reaction, using the calculated difference.

According to a seventh aspect of the present invention there is provided a computer readable medium storing computer executable instructions for performing steps of identifying transition points in a chemical reaction, the steps comprising: a) receiving a plurality of values of a physical property of the chemical reaction, b) calculating a function having a line of best fit with a same slope as a linear function connecting two of the received values, the two values pertaining to a start and end of a time period, c) calculating a difference between the calculated function and a plurality of the received values pertaining to the time period having the start and end, and d) identifying at least one transition point of the chemical reaction, using the calculated difference.

According to an eighth aspect of the present invention there is provided a system for identifying transition points in a chemical reaction, the apparatus comprising: a chemical reaction apparatus, comprising at least one sensor configured to measure a plurality of values of a physical property of a chemical reaction, a property value receiver, associated with the chemical reaction apparatus, configured to receive the plurality of values of the physical property of the chemical reaction, a function calculator, associated with the property value receiver, configured to calculate a function having a line of best fit with a same slope as a linear function connecting two of the received values, the two values pertaining to a start and end of a time period, a difference calculator, associated with the function calculator, configured to calculate a difference between the calculated function and a plurality of the received values pertaining to the time period having the start and end, and a transition point identifier, associated with the difference calculator, configured to identify at least one transition point of the chemical reaction, using the calculated difference.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. The description taken with the drawings making apparent to those skilled in the art how the several forms of the invention may be embodied in practice.

In the drawings.

DESCRIPTION OF THE PREFERRED EMBODIMENTS

Figure 1:
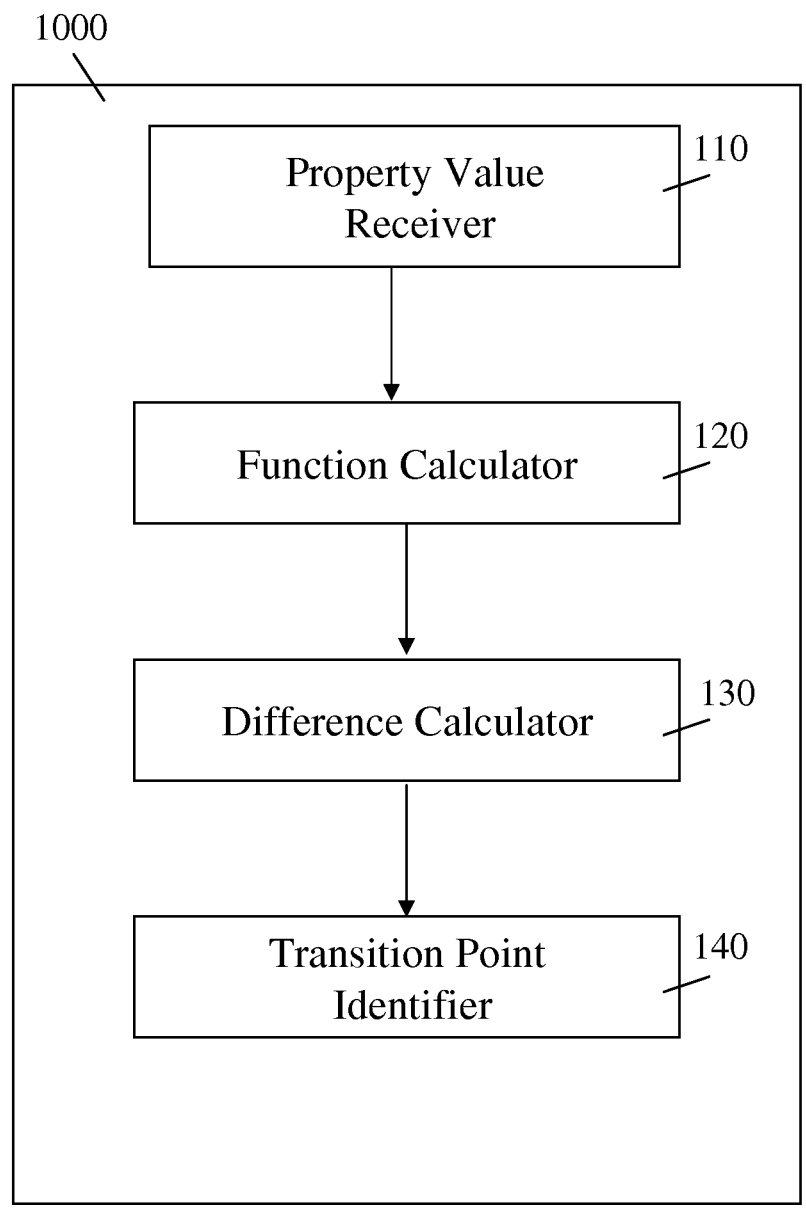
FIG. 1 is a block diagram schematically illustrating an apparatus for identifying transition points in a chemical reaction, according to an exemplary embodiment of the present invention.

The present embodiments comprise a system and method for identifying transition points in a chemical reaction.

For example, a point of exponential growth of the chemical reaction's product and a point where growth of the product begins to slow to a halt are referred to as elbow points. The elbow points may be used to determine whether any reaction products have been produced, as well as to determine the magnitude of the chemical reaction, as described in further detail hereinabove.

According to an exemplary embodiment of the present invention, one or more transition points of a chemical reaction are identified, using a function having a line of best fit with a same slope as a linear function which connects two values (say points) of a physical property of the chemical reaction. For example, the values may be photometric values measured by sensors installed in proximity of a PCR reaction chamber, during a PCR process. The two values pertain to a start and an end of a time period of the chemical reaction (say the start and end of the PCR chemical reaction), respectively.

Optionally, the function is calculated by randomly (say by trial and error) selecting points in proximity of the linear function, say points restricted to a predefined distance from the linear function, while verifying that the function's line of best fit is parallel to the linear function, as described in further detail hereinbelow.

Optionally, the function is calculated by compositing and adjusting one or more sinusoidal, polynomial, or any other functions, while verifying that the calculated function's line of best fit is parallel to the linear function which connects the two points.

The line of best fit may be calculated using PCA (Principal Component Analysis) applied on the calculated function (say on points of the calculated function), using linear regression applied on the calculated function (say the points), etc., as known in the art.

In order to identify the transition points, there is calculated a difference between the calculated function and values of the physical property between the two values connected by the linear function (i.e. values measured between the start and end of the time period).

The calculated difference serves to emphasize phase transitions of the chemical reaction, which are non-linear, and are usually substantially exponential.

The phase transitions are emphasized since the linear function's slope, and hence the slope of the line of best fit of the calculated function, represent a nearly average rate of the chemical reaction during the time period between the two points that the linear function connects.

That is to say that a comparison with the linear function, or with a function, which has a line of best fit parallel to the linear function, may help identify the transition points of the chemical reaction. The transition points are thus characterized, based on a reaction rate which substantially deviates from the nearly average rate of the chemical reaction, as represented by the slope of the linear function and the line of best fit of the calculated function.

Having identified the transition point(s) of the chemical reaction, a system according to an exemplary embodiment, may provide a user (say a laboratory technician who operates a PCR Apparatus) with monitoring data based on the identified transition point(s).

The system according to an exemplary embodiment, may further initiate a control operation (say cooling of a chamber where the chemical reaction takes place) upon identifying the transition point(s), etc., in real time, as described in further detail hereinbelow.

The principles and operation of a system and method according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Reference is now made to FIG. 1, which is a block diagram schematically illustrating an apparatus for identifying transition points in a chemical reaction, according to an exemplary embodiment of the present invention.

Apparatus 1000 for identifying transition points in a chemical reaction may be implemented using electric circuits, computer instructions, etc. The apparatus 1000 may be implemented on an electronic computing device such as a dedicated computer, a computer chip connectable to a laboratory device (say to a PCR apparatus, as known in the art) or installable thereon, a computerized controller (say a computerized controller used in a chemical factory), an electric circuit, etc.

Optionally, the chemical reaction is a Polymerase Chain Reaction (PCR), say a Quantitative Fluorescent Polymerase Chain Reaction (QF-PCR).

The apparatus 1000 includes a property value receiver 110.

The property value receiver 110 receives values of a physical property of the chemical reaction.

Optionally, the property value receiver 110 receives the physical property values from thermometric sensors installed inside a chamber where the chemical reaction takes place, from photometric sensors deployed in proximity to the chamber, or from other devices, as described in further detail hereinbelow.

For example, the chemical reaction may be a Quantitative Fluorescent Polymerase Chain Reaction (QF-PCR). The Quantitative Fluorescent Polymerase Chain Reaction is subjected to photometric measurements of light emitted from the QF-PCR reaction chamber, during the chemical reaction inside the QF-PCR chamber. The photometric measurement's values are then input, in real time, to the property value receiver 110.

Optionally, the apparatus 1000 further includes one or more photometric measurement devices, say photo sensors installed in proximity to a chamber where the chemical reaction takes place. The photometric measurement devices are in communication with the property value receiver 110, for providing the property value receiver 110 with the values, as measured by the photometric measurement devices while the chemical reaction progresses.

The apparatus 1000 further includes a function calculator 120.

The function calculator 120 is in communication with the property value receiver 110.

The function calculator 120 calculates a function having a line of best fit with a same slope as a linear function connecting two of the received values. The two values pertain to a start and end of a time period, as described in further detail hereinbelow That is to say that the calculated function's line of best fit either parallels, or coincides with the linear function which connects the two points.

Optionally, the start and end points pertain to a start and end of the chemical reaction, respectively.

Optionally, the start point pertains to a point immediately after a point which pertains to the start of the chemical reaction.

Optionally, the end point pertains to a point immediately before a point which pertains to the start of the chemical reaction.

The time period may be a time period the chemical reaction is supposed to last for, a time period when a part of the chemical reaction takes place, a time period long enough for the reaction to happen, a time period spanning several cycles of the chemical reaction, etc.

Optionally, the function calculator 120 further allows a user of the apparatus 1000, to define the start and end of the time period, say by inputting data defining the time period in absolute (say from 10:00 PM to 10:15 PM) or relative (say 15 minutes from start) terms.

Optionally, the function calculator 120 calculates the function by randomly (say by trial and error) selecting points in proximity of the linear function, say points restricted to a predefined distance from the linear function, while verifying that the function's line of best fit has a same slope as the linear function, as described in further detail hereinbelow.

Optionally, the distance is defined by a user of the apparatus 1000, say using a dedicated user interface which graphically presents relevant data (such as historic data pertaining to results of similar chemical reactions), and which may be operated by the user, for defining the distance.

Optionally, the function calculator 120 calculates the function by compositing and adjusting one or more sinusoidal, polynomial, or any other functions, while verifying that the calculated function's line of best fit has a same slope as the linear function which connects the two points.

The line of best fit may be calculated using PCA (Principal Component Analysis) applied on the calculated function (say on points of the calculated function), using linear regression applied on the calculated function (say the points), etc., as known in the art.

Optionally, the calculated function is a non-linear function.

Optionally, the calculated function is a linear function parallel to the linear function which connects the two points, but different from the linear function which connects the two points.

In a first example, the calculated function is a linear function which parallels the linear function which connects the two points, but intercepts the vertical axis (i.e. a Y-axis which represents the physical property values) in a point higher than the linear function which connects the two points.

In a second example, the calculated function is a linear function which parallels the linear function which connects the two points, but intercepts the vertical axis (i.e. a Y-axis which represents the physical property values) in a point lower than the linear function which connects the two points Optionally, the function calculator 120 further verifies that all points of the calculated function are within a predefined distance from the calculated function's line of best fit, say a distance selected by a user of the apparatus 1000, as described in further detail hereinabove.

Optionally, the function calculator 120 further verifies that all points of the calculated function are within a fixed distance from the line of best fit.

Optionally, the fixed distance is derived from known detection limits characteristic of the chemical reaction, of an apparatus (say a chamber with sensors) the chemical reactions occurs in, etc.

In one example, the fixed distance equals a mathematical product of three times a standard deviation of a value of the physical property, as measured by the apparatus in which the chemical reaction occurs, for a negative control sample (say a matrix without analytes), and five times a dilution factor characteristic of the chemical reaction, as described in further detail and illustrated in Appendix-A, hereinbelow.

Typically, the dilution factor characteristic of the chemical reaction is attributed to dilution, concentration, loss of material in preliminary stages of the chemical reaction, etc. For example, a part of the reaction's reagents may be consumed in preliminary stages of heating, due to adherence to a reaction chamber's walls, etc., as described in further detail and illustrated in Appendix-A, hereinbelow.

The calculated function may include, but is not limited to exemplary functions graphically illustrated using FIG. 6-7 hereinbelow.

The apparatus 1000 further includes a difference calculator 130, in communication with the function calculator 120.

The difference calculator 130 calculates a difference between the calculated function and two (or more) of the received values that pertain to the time period. For example, the difference calculator 130 may calculate a difference between the calculated function and a curve based on the received values, over a time period of the chemical reaction (or a segment thereof), as described in further detail hereinbelow.

Apparatus 1000 further includes a transition point identifier 140, in communication with the difference calculator 130.

The transition point identifier 140 identifies one or more transition points of the chemical reaction, using the calculated difference, as described in further detail hereinbelow. For example, the transition point identifier 140 may identify the transition points, by finding the points where the difference between the calculated function and the received values is maximal, minimal, etc.

Optionally, at least one of the transition points identified by the transition point identifier 140 is a point in time of the chemical reaction, when the value of the physical property starts increasing substantially exponentially.

Optionally, at least one of the transition points identified by the transition point identifier 140 is a point in time of the chemical reaction, when the value of the physical property stops increasing substantially exponentially.

Optionally, at least one of the transition points identified by the transition point identifier 140 is a point in time of the chemical reaction, when the value of the physical property starts decreasing substantially exponentially.

Optionally, at least one of the transition points identified by the transition point identifier 140 is a point in time of the chemical reaction, when the value of the physical property stops decreasing substantially exponentially.

Optionally, the apparatus 1000 also includes a phase indicator, in communication with the transition point identifier 140.

Optionally, when the transition point is identified, the phase indicator indicates a beginning of a phase of the chemical reaction, an end of a phase of the chemical reaction, an end of a preliminary stabilization phase of the chemical reaction, or any combination thereof.

Optionally, the apparatus 1000 further includes a control operation initiator, in communication with the transition point identifier 140.

When the transition point is identified, the control operation initiator initiates a control operation. The control operation may include, but is not limited to: initiating cooling of a chamber where the chemical reaction takes place, opening of a pressure valve of a reaction chamber, instructing a PCR Robot to stop rotating, etc., as known in the art.

Optionally, the apparatus 1000 further includes a monitoring data generator, in communication with the transition point identifier 140, as described in further detail hereinbelow.

The monitoring data generator generates monitoring data based on the identified transition point(s).

Optionally, the monitoring data generator further presents the generated data to a user, say using a computer screen, an SMS (Short Messages Service) message on a cellular phone used by the user, a message on a portable computer device such as a personal digital assistant (PDA), or a notebook computer, etc.

Figure 2:
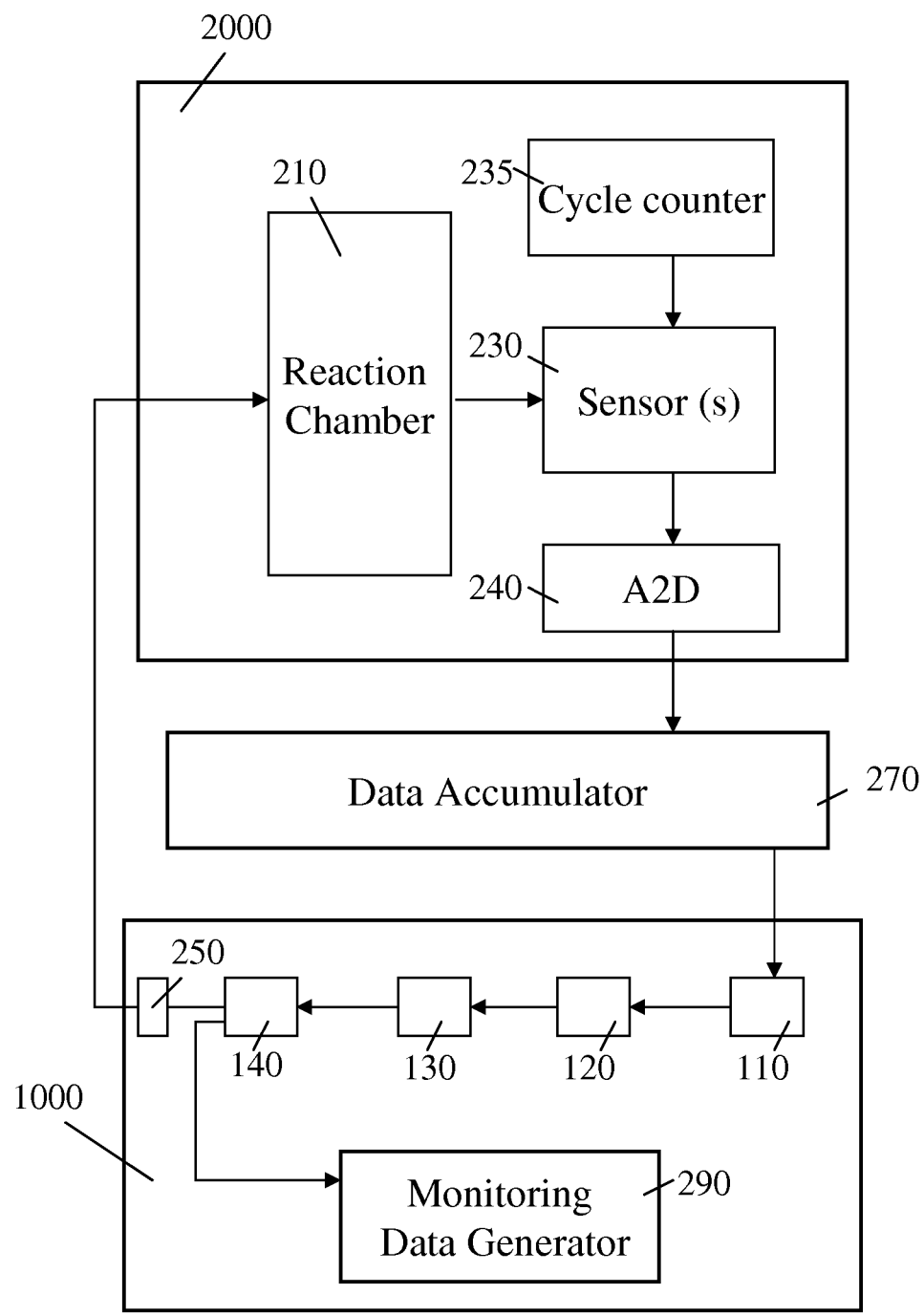
FIG. 2 is a block diagram schematically illustrating a system for identifying transition points in a chemical reaction, according to an exemplary embodiment of the present invention.

Reference is now made to FIG. 2, which is a block diagram schematically illustrating a system for identifying transition points in a chemical reaction, according to an exemplary embodiment of the present invention.

A system according to an exemplary embodiment of the present invention includes a chemical reaction apparatus 2000.

Optionally, the chemical reaction apparatus 2000 includes a reaction chamber 210, where a chemical reaction (say PCR) takes place.

Optionally, the chemical reaction apparatus 2000 further includes one or more sensors 230, for measuring values of a physical property of the chemical reaction.

For example, the sensors 230 may be photometric sensors installed in proximity of the reaction chamber 210. The photometric sensors measure intensity of light emitted from the reaction chamber 210, as the chemical reactions progresses.

The photometric sensors measure the emission of light from the reaction chamber, using standard fluorescence methods, as known in the art.

The chemical reaction apparatus 2000 may further include a cycle counter 235, connected to the sensors 230. The cycle counter 235 instructs the sensors 230 to take measurement of the physical property, say once in an interval of time. Optionally, the interval of time is predefined by a user, as known in the art.

The chemical reaction apparatus 2000 may further include an Analog-to-Digital (A2D) converter 240, connected to the sensors 230. The Analog-to-Digital (A2D) converter 240 converts the measured values of the physical property of the chemical reaction to a digital format.

System 1000 further includes a data accumulator 270, in communication with the A2D converter 240.

The data accumulator 270 receives the measured values from the A2D converter 240, and stores the measured values.

The data accumulator 270 may include, but is not limited to a CD-ROM, a Flash Memory, a RAM (Random Access Memory), etc., as known in the art.

The system may further include apparatus 1000, as described in further detail hereinabove.

Apparatus 1000 may be implemented using electric circuits, computer instructions, etc. The apparatus 1000 may be implemented on an electronic computing device such as a dedicated computer, a computer chip connected to the chemical reaction apparatus 2000 or installed thereon, a computerized controller connected to the chemical reaction apparatus 2000 or installed thereon, an electric circuit, etc.

Optionally, the chemical reaction is a Polymerase Chain Reaction (PCR), say a Quantitative Fluorescent Polymerase Chain Reaction (QF-PCR), as described in further detail hereinabove.

Apparatus 1000 includes a property value receiver 110, in communication with the data accumulator 270.

The property value receiver 110 receives values of a physical property of the chemical reaction, from the data accumulator 270, say in real time, as the reaction progresses, as described in further detail hereinabove.

The apparatus 1000 further includes a function calculator 120.

The function calculator 120 is in communication with the property value receiver 110.

The function calculator 120 calculates a function having a line of best fit with a same slope as a linear function connecting two of the received values. The two values pertain to a start and end of a time period, as described in further detail hereinbelow.

That is to say that the line of best fit either parallels, or coincides with the linear function which connects the two points.

Optionally, the start and end points pertain to a start and end of the chemical reaction, respectively.

Optionally, the start point pertains to a point immediately after a point which pertains to the start of the chemical reaction.

Optionally, the end point pertains to a point immediately before a point which pertains to the start of the chemical reaction.

The time period may be a time period the chemical reaction is supposed to last for, a time period when a part of the chemical reaction takes place, a time period long enough for the reaction to happen, a time period spanning several cycles of the chemical reaction, etc.

Optionally, the function calculator 120 further allows a user of the apparatus 1000, to define the start and end of the time period, say by inputting data defining the time period, as described in further detail hereinabove.

Optionally, the function calculator 120 calculates the function by randomly (say by trial and error) selecting points in proximity of the linear function, say points restricted to a predefined distance from the linear function, while verifying that the function's line of best fit has a same slope as the linear function, as described in further detail hereinbelow.

Optionally, the distance is defined by a user of the apparatus 1000, say using a dedicated user interface which may be operated by the user, for defining the distance, as described in further detail hereinabove.

Optionally, the function calculator 120 calculates the function by compositing and adjusting one or more sinusoidal, polynomial, or any other functions, while verifying that the calculated function's line of best fit has a same slope as the linear function which connects the two points.

The line of best fit may be calculated using PCA (Principal Component Analysis) applied on the calculated function (say on points of the calculated function), using linear regression applied on the calculated function (say the points), etc., as known in the art.

Optionally, the calculated function is a non-linear function.

Optionally, the calculated function is a linear function parallel to the linear function which connects the two points, but different from the linear function which connects the two points.

For example, the calculated function may be a linear function which intercepts the vertical axis (i.e. a Y-axis which represents the physical property values) in a point higher than the linear function which connects the two points, a function which intercepts the vertical axis in a point lower than the linear function which connects the two points, etc, as described in further detail hereinabove.

Optionally, the function calculator 120 further verifies that all points of the calculated function are within a predefined distance from the calculated function's line of best fit (say a distance selected by a user of the apparatus 1000, as described in further detail hereinabove).

Optionally, the function calculator 120 further verifies that all points of the calculated function are within a fixed distance from the line of best fit.

Optionally, the fixed distance is derived from known detection limits characteristic of the chemical reaction, of the apparatus 2000, of the chamber 210, of the sensors 230, etc., or any combination thereof.

In one example, the fixed distance equals a mathematical product of three times a standard deviation of a value of the physical property, as measured by the apparatus in which the chemical reaction occurs, for a negative control sample (say a matrix without analytes), and five times a dilution factor characteristic of the chemical reaction, as described in further detail and illustrated in Appendix-A, hereinbelow.

Typically, the dilution factor characteristic of the chemical reaction is attributed to dilution, concentration, or loss of material in preliminary stages of the chemical reaction. For example, a part of the reaction's reagents may be consumed in preliminary stages of heating, due to adherence to a reaction chamber's walls, etc., as described in further detail and illustrated in Appendix-A, hereinbelow.

The calculated function may include, but is not limited to exemplary functions graphically illustrated using FIG. 6-7 hereinbelow.

The apparatus 1000 further includes a difference calculator 130, in communication with the function calculator 120.

The difference calculator 130 calculates a difference between the calculated function and two (or more) of the received values that pertain to the time period. For example, the difference calculator 130 may calculate a differences between the calculated function and a curve based on the received values, over a time period of the chemical reaction (or a segment thereof), as described in further detail hereinbelow.

Apparatus 1000 further includes a transition point identifier 140, in communication with the difference calculator 130.

The transition point identifier 140 identifies one or more transition points of the chemical reaction, using the calculated difference, as described in further detail hereinbelow. For example, the transition point identifier 140 may identify the transition points, by finding the points where the difference between the calculated function and the received values is maximal, minimal, etc.

Optionally, at least one of the transition points identified by the transition point identifier 140 is a point in time of the chemical reaction, when the value of the physical property starts increasing substantially exponentially.

Optionally, at least one of the transition points identified by the transition point identifier 140 is a point in time of the chemical reaction, when the value of the physical property stops increasing substantially exponentially.

Optionally, at least one of the transition points identified by the transition point identifier 140 is a point in time of the chemical reaction, when the value of the physical property starts decreasing substantially exponentially.

Optionally, at least one of the transition points identified by the transition point identifier 140 is a point in time of the chemical reaction, when the value of the physical property stops decreasing substantially exponentially.

Optionally, the apparatus 1000 further includes a control operation initiator 250, in communication with the transition point identifier 140.

When the transition point is identified, the control operation initiator 250 initiates a control operation. The control operation may include, but is not limited to: initiating cooling of a chamber 210 where the chemical reaction takes place, opening of a pressure valve of the reaction chamber 210, instructing a PCR Robot to stop rotating, etc., as known in the art.

Optionally, the apparatus 1000 further includes a monitoring data generator 290, in communication with the transition point identifier 140. The monitoring data generator 290 generates monitoring data based on the identified transition point.

Optionally, the monitoring data generator 290 further presents the generated data to a user, say using a computer screen, an SMS (Short Messages Service) message on a cellular phone used by the user, a message on a portable computer device such as a personal digital assistant (PDA), or a notebook computer, etc.

Optionally, the monitoring data generator 290 further provides decision support services to the user (say by presenting the generated data to the user in a spreadsheet format such as a Microsoft© Excel spreadsheet).

Figure 3:
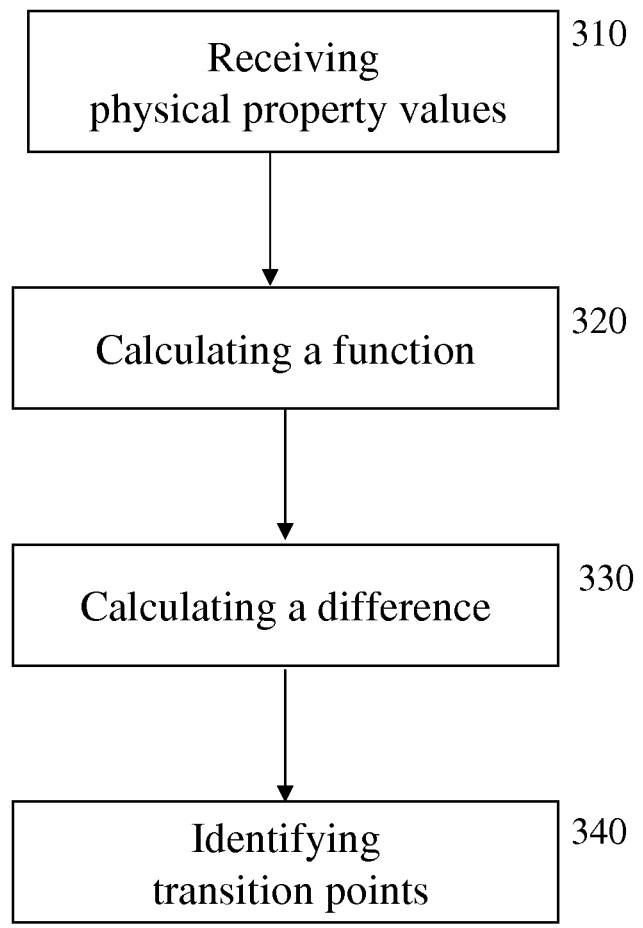
FIG. 3 is a flowchart schematically illustrating a method for identifying transition points in a chemical reaction, according to an exemplary embodiment of the present invention.

Reference is now made to FIG. 3, which is a flowchart schematically illustrating a method for identifying transition points in a chemical reaction, according to an exemplary embodiment of the present invention.

According to an exemplary embodiment, an exemplary method for identifying transition points in a chemical reaction may be implemented using electric circuits, computer instructions, etc. The method may be implemented on an electronic computing device such as a dedicated computer, a computer chip connectable to a laboratory device (say to a PCR apparatus, as known in the art) or installable thereon, a computerized controller (say a computerized controller used in a chemical factory), an electric circuit, etc., as described in further detail hereinabove.

Optionally, the chemical reaction is a Polymerase Chain Reaction (PCR), say a Quantitative Fluorescent Polymerase Chain Reaction (QF-PCR).

In the exemplary method, there are received 310 values of a physical property of the chemical reaction, by the physical property receiver 110, as described in further detail hereinabove.

Optionally, the physical property values are received from thermometric sensors installed inside a chamber where the chemical reaction takes place, from photometric sensors deployed in proximity to the chamber, or from other measurement devices, as described in further detail hereinabove.

For example, the chemical reaction may be a Quantitative Fluorescent Polymerase Chain Reaction (QF-PCR). The Quantitative Fluorescent Polymerase Chain Reaction is subjected to photometric measurements of light emitted from the QF-PCR reaction chamber, during the chemical reaction inside the QF-PCR chamber. The photometric measurement's values are then received 310, say by the property value receiver 110, as described in further detail hereinabove.

Next, there is calculated 320 a function having a line of best fit with a same slope as a linear function connecting two of the received values, say using the function calculator 120, as described in further detail hereinabove. The two values pertain to a start and end of a time period, as described in further detail hereinbelow.

That is to say that the line of best fit either parallels, or coincides with the linear function which connects the two points.

Optionally, the start and end points pertain to a start and end of the chemical reaction, respectively.

Optionally, the start point pertains to a point immediately after a point which pertains to the start of the chemical reaction.

Optionally, the end point pertains to a point immediately before a point which pertains to the start of the chemical reaction.

The time period may be a time period the chemical reaction is supposed to last for, a time period when a part of the chemical reaction takes place, a time period long enough for the reaction to happen, a time period spanning several cycles of the chemical reaction, etc.

Optionally, a user of the apparatus 1000 is allowed to define the start and end of the time period, say by inputting data defining the time period in absolute (say from 10:00 PM to 10:15 PM) or relative (say 15 minutes from start) terms.

Optionally, the function is calculated 320 by randomly (say by trial and error) selecting points in proximity of the linear function, say points restricted to a predefined distance from the linear function, while verifying that the function's line of best fit has a same slope as the linear function, as described in further detail hereinbelow.

Optionally, the distance is defined by a user of apparatus 1000, say using a dedicated user interface which may be operated by the user, for defining the distance, as described in further detail hereinabove.

Optionally, the function is calculated 320 by compositing and adjusting one or more sinusoidal, polynomial, or any other functions, while verifying that the calculated function's line of best fit has a same slope as the linear function which connects the two points.

The line of best fit may be calculated using PCA (Principal Component Analysis) applied on the calculated function (say on points of the calculated function), using linear regression applied on the calculated function (say the points), etc., as known in the art.

Optionally, the calculated 320 function is a non-linear function.

Optionally, the calculated 320 function is a linear function parallel to the linear function which connects the two points, but different from the linear function which connects the two points.

For example, the calculated 320 function may be a linear function which intercepts the vertical axis (i.e. a Y-axis which represents the physical property values) in a point higher than the linear function which connects the two points, a function which intercepts the vertical axis in a point lower than the linear function which connects the two points, etc, as described in further detail hereinabove.

Optionally, as a part of the calculation 320, there is further verified that all points of the calculated 320 function are within a predefined distance from the calculated 320 function's line of best fit (say a distance selected by an operator of apparatus 1000).

Optionally, as a part of the calculation 320, there is further verified that all points of the calculated 320 function are within a fixed distance from the line of best fit.

Optionally, the fixed distance is derived from known detection limits characteristic of the chemical reaction, of an apparatus (say a chamber with sensors) the chemical reactions occurs in, etc.

In one example, the fixed distance equals a mathematical product of three times a standard deviation of a value of the physical property, as measured by the apparatus in which the chemical reaction occurs, for a negative control sample (say a matrix without analytes), and five times a dilution factor characteristic of the chemical reaction, as described in further detail and illustrated in Appendix-A, hereinbelow.

Typically, the dilution factor characteristic of the chemical reaction is attributed to dilution, concentration, or loss of material in preliminary stages of the chemical reaction. For example, a part of the reaction's reagents may be consumed in preliminary stages of heating, due to adherence to a reaction chamber's walls, etc., as described in further detail and illustrated in Appendix-A, hereinbelow.

The calculated 320 function may include, but is not limited to exemplary functions graphically illustrated using FIG. 6-7 hereinbelow.

Next, there is calculated 330 a difference between the calculated 320 function and two (or more) of the received values that pertain to the time period. For example, the difference calculator 130 may calculate 330 a difference between the calculated 320 function and a curve based on the received values, over a time period of the chemical reaction (or a segment thereof), as described in further detail hereinbelow.

Finally, there is identified 340 one or more transition points of the chemical reaction, using the calculated difference, as described in further detail hereinbelow. For example, the transition point identifier 140 may identify 340 the transition points, by finding the points where the difference between the calculated 320 function and the received values is maximal, minimal, etc.

Optionally, at least one of the identified 340 transition points is a point in time of the chemical reaction, when the value of the physical property starts increasing substantially exponentially.

Optionally, at least one of the identified 340 transition points is a point in time of the chemical reaction, when the value of the physical property stops increasing substantially exponentially.

Optionally, at least one of the identified 340 transition points is a point in time of the chemical reaction, when the value of the physical property starts decreasing substantially exponentially.

Optionally, at least one of the identified 340 transition points is a point in time of the chemical reaction, when the value of the physical property stops decreasing substantially exponentially.

Optionally, when the transition point is identified 340, there is indicated a beginning of a phase of the chemical reaction, an end of a phase of the chemical reaction, an end of a preliminary stabilization phase of the chemical reaction, or any combination thereof.

Optionally, when the transition point is identified 340, there is initiated a control operation. The control operation may include, but is not limited to: initiating cooling of a chamber where the chemical reaction takes place, opening of a pressure valve of a reaction chamber, instructing a PCR Robot to stop rotating, etc., as known in the art.

Optionally, there is further generated monitoring data based on the identified transition point.

Optionally, the monitoring data is presented to a user. For example, the monitoring data may be presented on a computer screen, in an SMS (Short Messages Service) message on a cellular phone used by the user, in a message on a portable computer device such as a personal digital assistant (PDA), or a notebook computer, etc.

Reference is now made to FIGS. 4A, 4B, 4C, 4D and 4E, which are exemplary graphs, illustrating an exemplary scenario of identifying transition points in a chemical reaction, according to an exemplary embodiment of the present invention.

Figure 4A:
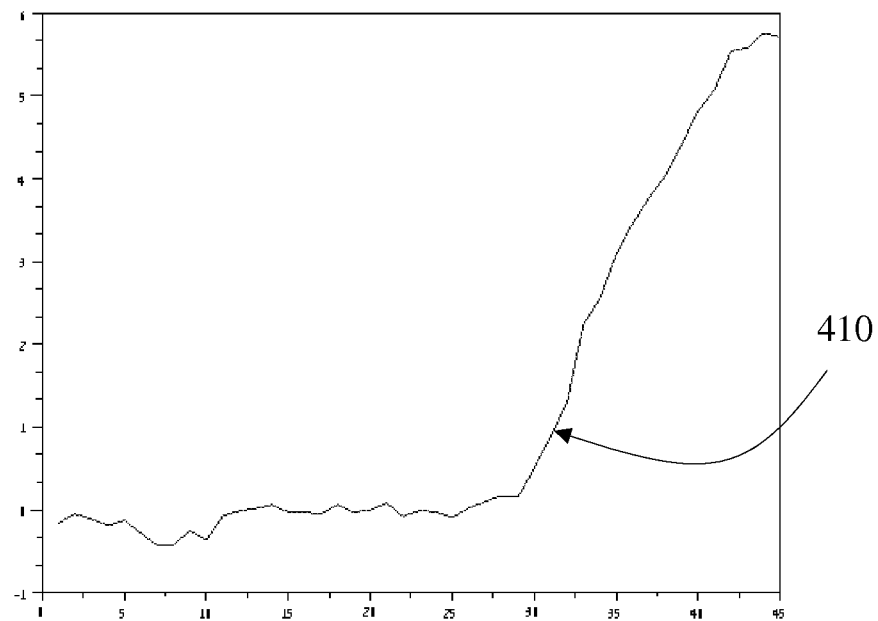
FIGS. 4A, 4B, 4C, 4D and 4E are exemplary graphs, illustrating an exemplary scenario of identifying transition points in a chemical reaction, according to an exemplary embodiment of the present invention.

FIG. 4A graphically shows an exemplary curve 410, which represents values measured during a time period of a chemical reaction (say values received using the property value receiver 110), as described in further detail hereinabove.

The x-axis corresponds to a time during the chemical reaction, whereas the y-axis represents the value of the property of the chemical reaction, say to photometric values measured by sensors installed in proximity of a PCR reaction chamber, during a PCR process, as described in further detail hereinabove. That is to say that each point on curve 410 represents the property's value at a single point in time of the chemical reaction.

Figure 4B:
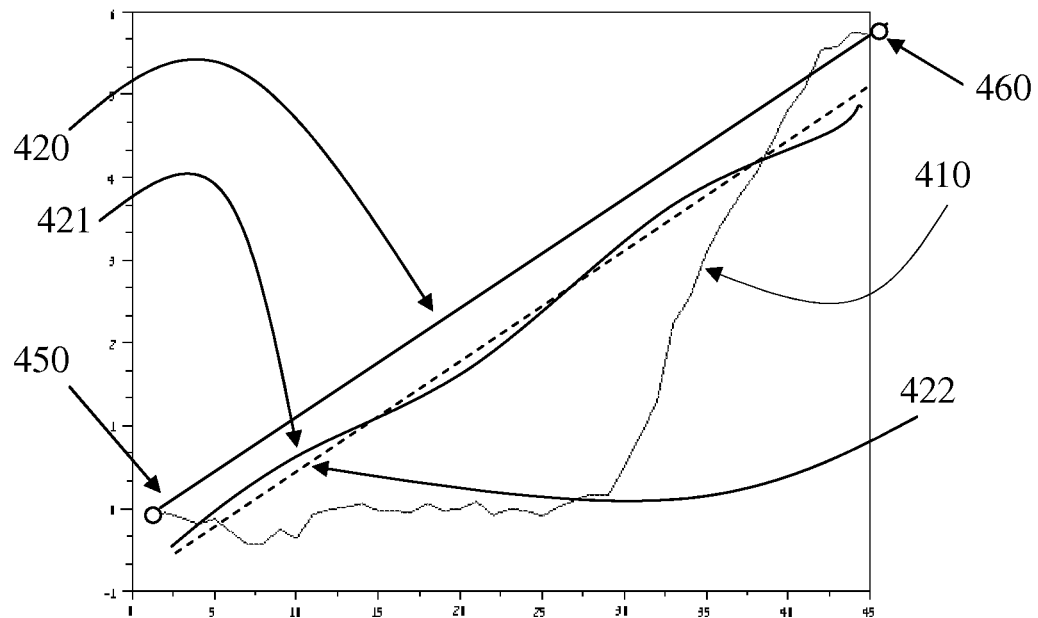

Reference is now made to FIG. 4B, which shows a curve of a first calculated function 421 having a line of best fit 422 with a same slope as a linear function 420 which connects a start point 450 and an end point 460 on curve 410. The first function 421 may be calculated by the function calculator 120, as described in further detail hereinabove.

Figure 4C:
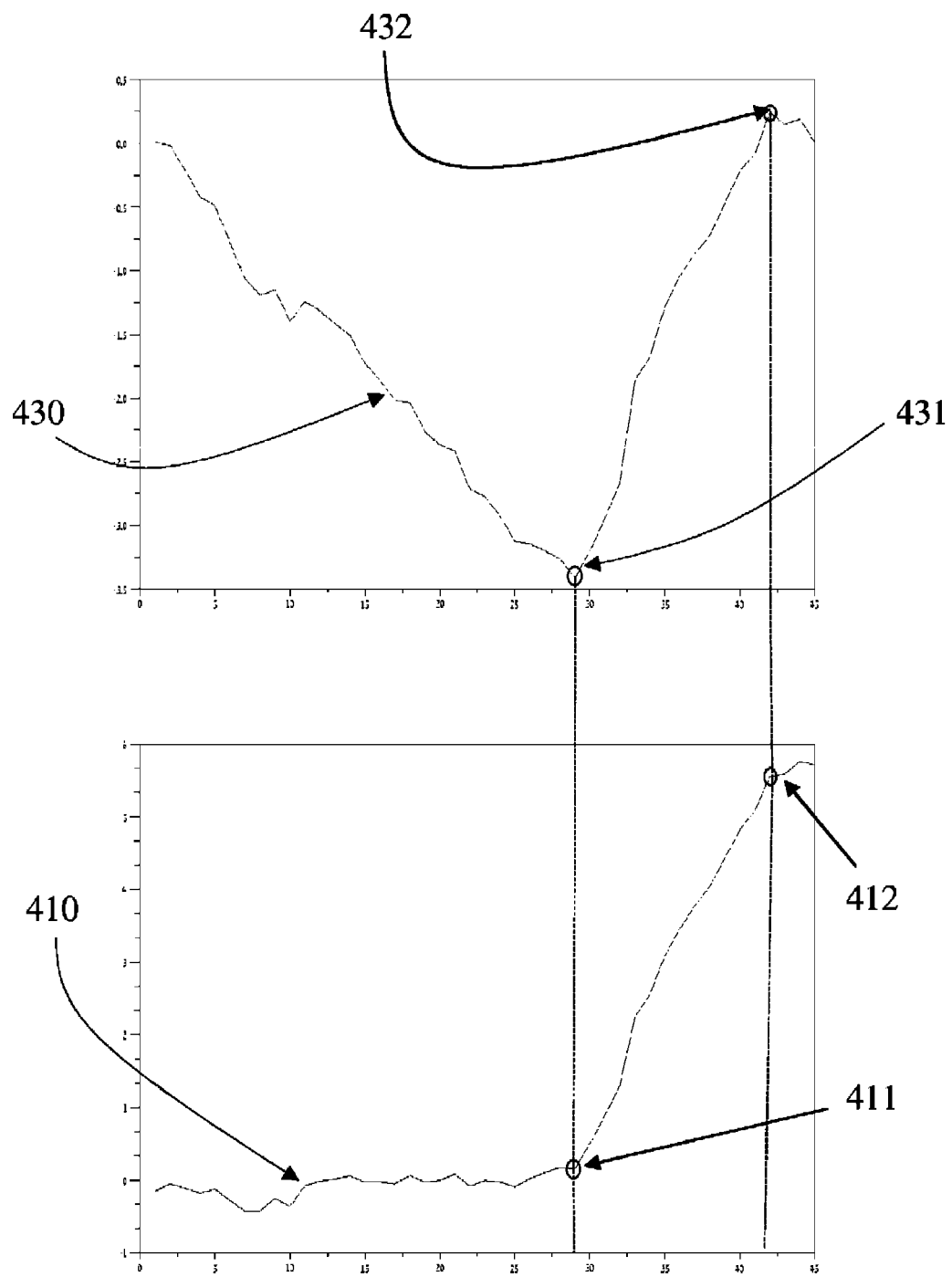

Reference is now made to FIG. 4C, which graphically shows a first difference curve 430. The first difference curve 430 represents the difference between the first calculated function 421 and curve 410. That is to say that the difference curve 430 represents the difference between the first calculated function 421 and the values of the physical property (say light emitted from a chemical chamber where the chemical reaction takes place) during the time period between the two points 450, 460.

Optionally, the difference represented by the first difference curve 430 is calculated by the difference calculator 130, as described in further detail hereinabove.

One or more extremum points of the difference curve 430, say a minimum point 431 and a maximum point 432, indicate the points in time of the chemical reaction (i.e. x-values) when transition points of the chemical reaction occur.

Consequently, points 411, 412 on curve 410, which correspond to the minimum point 431 and the maximum point 432, respectively, are identified as two transition points of the chemical reaction.

Optionally, in each of the transition points 411, 412, the value of the physical property starts decreasing substantially exponentially, stops decreasing substantially exponentially, starts increasing substantially exponentially, or stops increasing substantially exponentially, etc., as described in further detail hereinabove. That is to say that typically, in the transition point, the chemical reaction shifts from a substantially exponential phase into a substantially linear phase, or vise versa.

A method according to exemplary embodiment of the present invention may be applied on the whole chemical reaction (say on the whole of curve 410), and then, on specific parts of the chemical reaction (say on certain intervals of the curve 410).

Figure 4D:
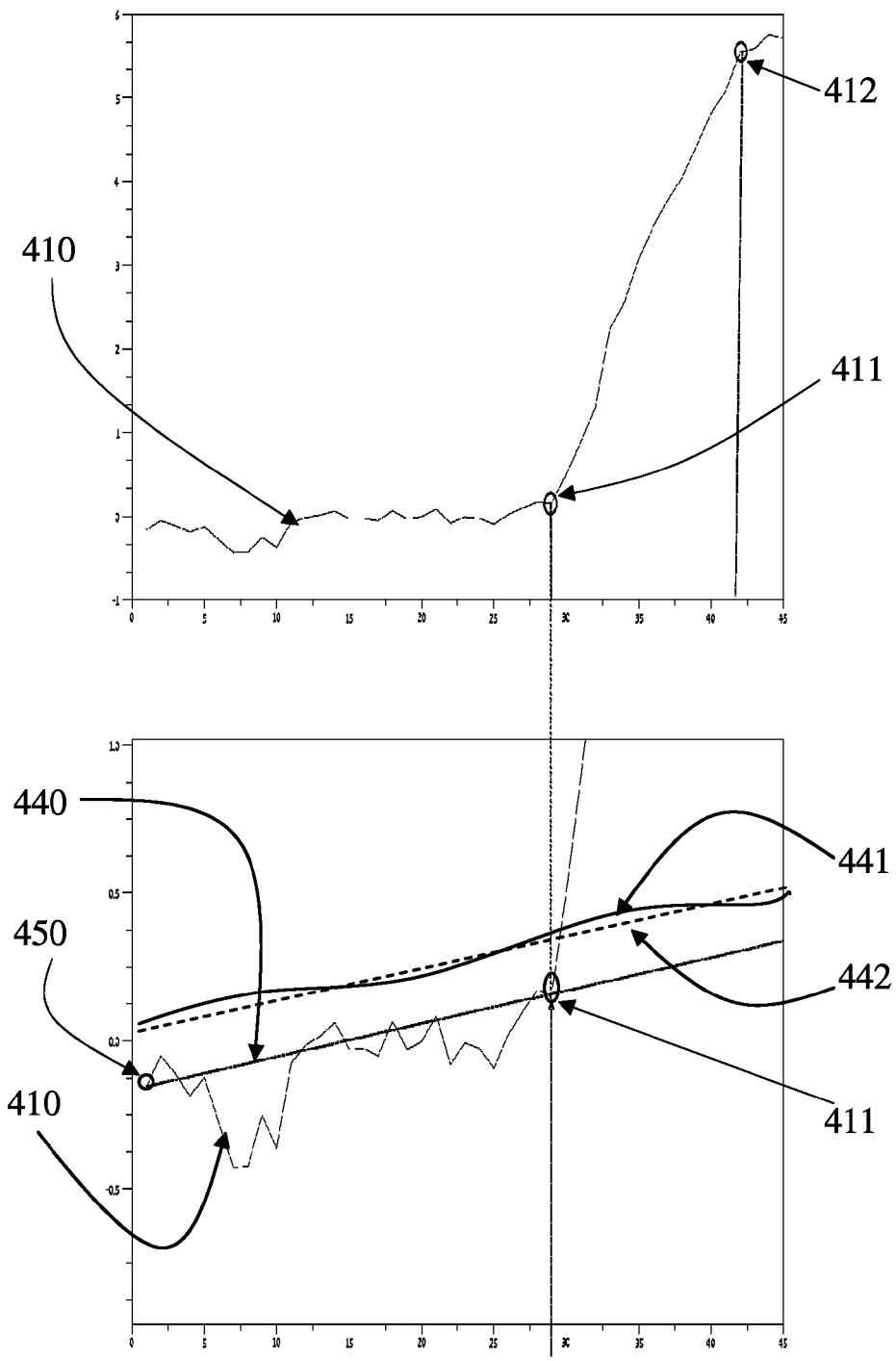

Reference is now made to FIG. 4D, which graphically shows a second calculated function 441, having a line of best fit 442 with a same slope as a linear function 440 which connects the first transition point 411 (which starts the exponential phase, which ends at the second transition point 412), and point 450.

The upper part of FIG. 4D shows curve 410 as it appears in FIG. 4A, whereas the lower part of FIG. 4D shows the curve 410 and the second calculated function 441 in a co-ordinate system where the y-coordinate is re-scaled, so as to illustrate more clearly the initial part of the curve 410.

Figure 4E:
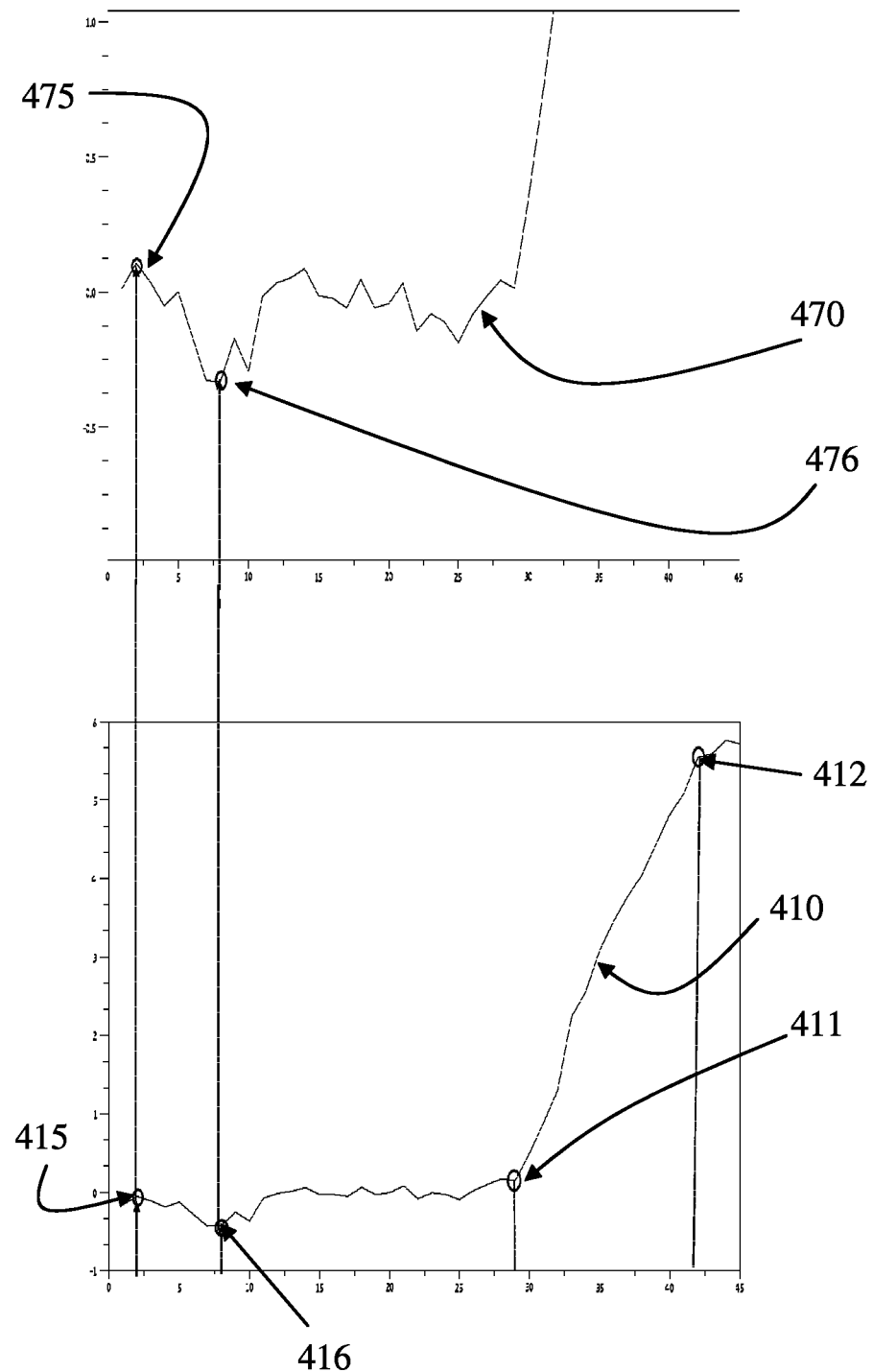

Reference is now made to FIG. 4E having an upper part which graphically shows a second difference curve 470 which represents the difference between the second calculated function 441 and the received values (i.e. curve 410).

Optionally, the difference represented by the second difference curve 470 is calculated by the difference calculator 130, as described in further detail hereinabove.

The second difference function 470 has a maximum 475 and a minimum 476.

The maximum 475 and minimum 476 are used to identify the chemical reaction's transition points 415, 416, on curve 410, as shown in the lower part of FIG. 4E.

In one example, transition points 415 corresponds to a start of a preliminary phase where ingredients are added to the reaction, and cause the physical property's values (say light emitted from the chemical reaction's chamber) to fluctuate. Transition point 416 may correspond to a phase where the added ingredients reach an even distribution in the reaction chamber, which causes the physical property to stabilize.

Figure 5:
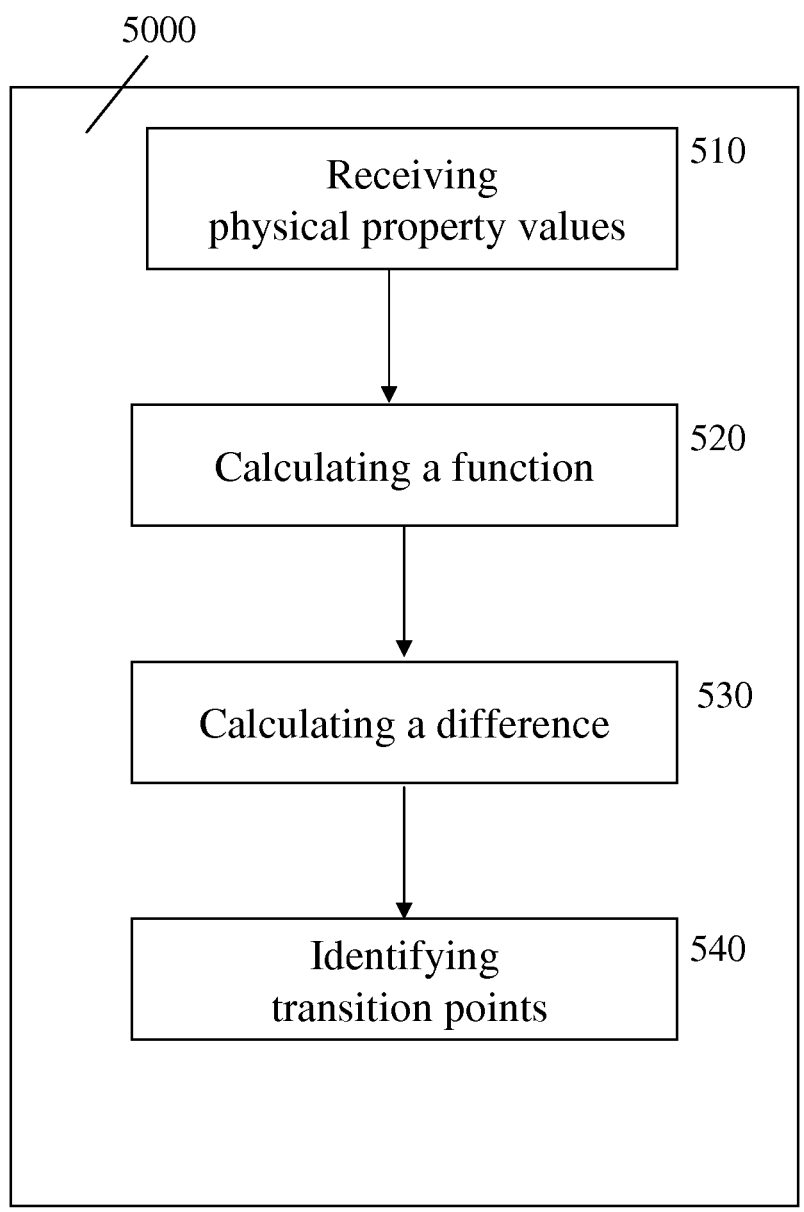
FIG. 5 is a block diagram schematically illustrating a computer readable medium storing computer executable instructions for performing steps of identifying transition points in a chemical reaction, according to an exemplary embodiment of the present invention.

Reference is now made to FIG. 5, which is a block diagram schematically illustrating a computer readable medium storing computer executable instructions for performing steps of identifying transition points in a chemical reaction, according to an exemplary embodiment of the present invention.

According to an exemplary embodiment of the present invention, there is provided a computer readable medium 5000 such as a CD-ROM, a USB-Memory, a Portable Hard Disk, a diskette, etc. The computer readable medium stores computer executable instructions, for performing steps of identifying transition points in a chemical reaction, according to an exemplary embodiment of the present invention.

Upon execution by a computer, the instructions receive 510 values of a physical property of the chemical reaction, as described in further detail hereinabove.

Optionally, the physical property values are received from thermometric sensors installed inside a chamber where the chemical reaction takes place, from photometric sensors deployed in proximity to the chamber, or from other measurement devices, as described in further detail hereinabove.

For example, the chemical reaction may be a Quantitative Fluorescent Polymerase Chain Reaction (QF-PCR). The Quantitative Fluorescent Polymerase Chain Reaction is subjected to photometric measurements of light emitted from the QF-PCR reaction chamber, during the chemical reaction inside the QF-PCR chamber.

The photometric measurement's values are then received 510, as described in further detail hereinabove.

Then, the instructions calculate 520 a function having a line of best fit with a same slope as a linear function connecting two of the received values. The two values pertain to a start and end of a time period, as described in further detail hereinbelow.

That is to say that the line of best fit either parallels, or coincides with the linear function which connects the two points.

Optionally, the start and end points pertain to a start and end of the chemical reaction, respectively.

Optionally, the start point pertains to a point immediately after a point which pertains to the start of the chemical reaction.

Optionally, the end point pertains to a point immediately before a point which pertains to the start of the chemical reaction.

The time period may be a time period the chemical reaction is supposed to last for, a time period when a part of the chemical reaction takes place, a time period long enough for the reaction to happen, a time period spanning several cycles of the chemical reaction, etc.

Optionally, using some of the instructions, a user is allowed to define the start and end of the time period, say by inputting data defining the time period, as described in further detail hereinabove.

Optionally, the function is calculated 520 by randomly (say by trial and error) selecting points in proximity of the linear function, say points restricted to a predefined distance from the linear function, while verifying that the function's line of best fit has a same slope as the linear function, as described in further detail hereinabove.

Optionally, the steps further include a step of allowing a user to define the distance, say using a graphical user interface, which graphically presents relevant data (such as historic data pertaining to results of similar chemical reactions) to the user, and may be operated by the user, for defining the distance.

Optionally, the function is calculated 520 by compositing and adjusting one or more sinusoidal, polynomial, or any other functions, while verifying that the calculated function's line of best fit has a same slop as the linear function which connects the two points.

The line of best fit may be calculated using PCA (Principal Component Analysis) applied on the calculated function (say on points of the calculated function), using linear regression applied on the calculated function (say the points), etc.

Optionally, the calculated 520 function is a non-linear function.

Optionally, the calculated 520 function is a linear function parallel to the linear function which connects the two points, but different from the linear function which connects the two points.

For example, the calculated 520 function may be a linear function which intercepts the vertical axis (i.e. a Y-axis which represents the physical property values) in a point higher than the linear function which connects the two points, a function which intercepts the vertical axis in a point lower than the linear function which connects the two points, etc.

Optionally, as a part of the calculation 520, there is further verified that all points of the calculated 520 function are within a predefined distance from the calculated 520 function's line of best fit (say a distance selected by a user, using the graphical user interface, as described in further detail hereinabove).

Optionally, as a part of the calculation 520, there is further verified that all points of the calculated 520 function are within a fixed distance from the line of best fit.

Optionally, the fixed distance is derived from known detection limits characteristic of the chemical reaction, of an apparatus (say a chamber with sensors) the chemical reactions occurs in, etc.

In one example, the fixed distance equals a mathematical product of three times a standard deviation of a value of the physical property, as measured by the apparatus in which the chemical reaction occurs, for a negative control sample (say a matrix without analytes), and five times a dilution factor characteristic of the chemical reaction, as described in further detail and illustrated in Appendix-A, hereinbelow.

Typically, the dilution factor characteristic of the chemical reaction is attributed to dilution, concentration, or loss of material in preliminary stages of the chemical reaction. For example, a part of the reaction's reagents may be consumed in preliminary stages of heating, due to adherence to a reaction chamber's walls, etc., as described in further detail and illustrated in Appendix-A, hereinbelow.

The calculated 520 function may include, but is not limited to exemplary functions graphically illustrated using FIG. 6-7 hereinbelow.

Next, the instructions calculate 530 a difference between the calculated 520 function and two (or more) of the received values that pertain to the time period. For example, the instructions may calculate a differences between the calculated 520 function and a curve based on the received values, over a time period of the chemical reaction (or a segment thereof), as described in further detail hereinbelow.

Finally, the instructions identify 540 one or more transition points of the chemical reaction, using the calculated difference, as described in further detail hereinbelow. For example, the instructions may identify 540 the transition points, by finding the points where the difference between the calculated 520 function and the received values is maximal, minimal, etc.

Optionally, when the transition point is identified 540, the instructions further indicate that a phase of the chemical reaction begins, that a phase of the chemical reaction ends, that a preliminary stabilization phase of the chemical reaction ends, etc.

Optionally, when the transition point is identified 540, the instructions further initiate a control operation. The control operation may include, but is not limited to: initiating cooling of a chemical reaction chamber, opening of a pressure valve of a chemical reaction chamber, instructing a PCR Robot to stop rotating, etc.

Optionally, the instructions further generate monitoring data based on the identified transition point.

Optionally, the instructions further present the monitoring data to a user. For example, the monitoring data may be presented on a computer screen, in an SMS (Short Messages Service) message on a cellular phone used by the user, in a message on a portable computer device such as a personal digital assistant (PDA), or a notebook computer, etc.

Figure 6:
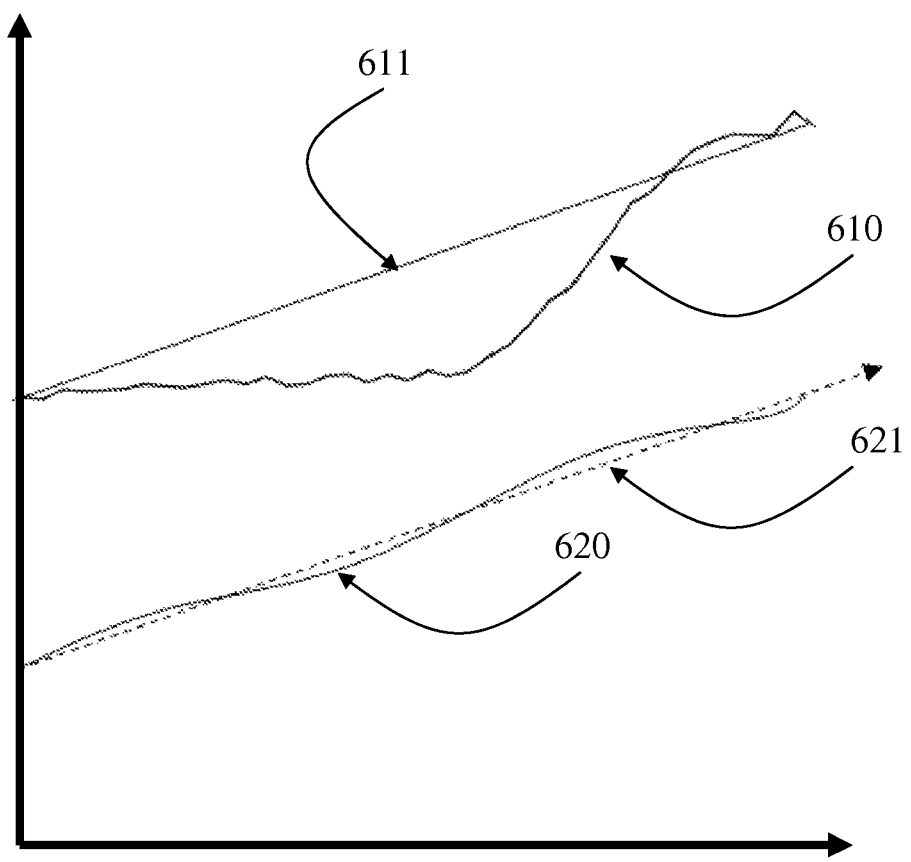
FIG. 6 is an exemplary graph, schematically illustrating a first exemplary calculated function, according to an exemplary embodiment of the present invention.

Reference is now made to FIG. 6, which is an exemplary graph, schematically illustrating a first exemplary calculated function, according to an exemplary embodiment of the present invention.

An exemplary non-linear function 620 depicted in FIG. 6, may be calculated by the function calculator 120, as described in further detail hereinabove.

The calculated function 620 has a line of best fit 621 with a same slope as a linear function 611 which connects two points of an exemplary reaction curve 610. The reaction curve 610 represents values measured during a time period of a chemical reaction. The two points mark the start and end of the time period, as described in further detail hereinabove.

Figure 7:
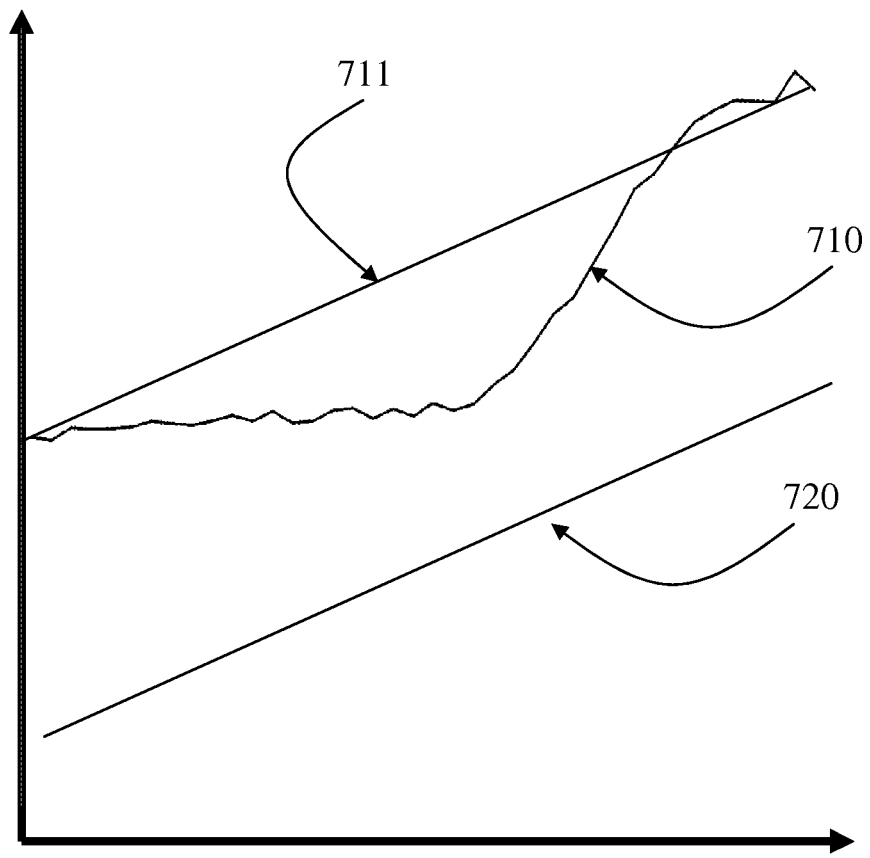
FIG. 7 is an exemplary graph, schematically illustrating a second exemplary calculated function, according to an exemplary embodiment of the present invention.

Reference is now made to FIG. 7, which is an exemplary graph, schematically illustrating a second exemplary calculated function, according to an exemplary embodiment of the present invention.

An exemplary linear function 720 depicted in FIG. 7, may be calculated by the function calculator 120, as described in further detail hereinabove.

The calculated function 720 is parallel to a linear function 711 which connects two points of an exemplary reaction curve 710. The reaction curve 710 represents values measured during a time period of a chemical reaction. The two points mark the start and end of the time period, as described in further detail hereinabove.

It is expected that during the life of this patent many relevant devices and systems will be developed and the scope of the terms herein, particularly of the terms "Polymerase Chain Reaction", "Quantitative Fluorescent Polymerase Chain Reaction" and "Fluorescence", is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

FURTHER DISCUSSION

Appendix-A

As described in further detail hereinabove, in some exemplary embodiments of the present invention, the points of the calculated 320 function may deviate from the calculated 320 function's line of best fit, provided each point is within a fixed distance from the line of best fit.

In one example, the fixed distance equals a mathematical product of three times a standard deviation of a value of the physical property, as measured by the apparatus in which the chemical reaction occurs, for a negative control sample (say a matrix without analytes), and five times a dilution factor characteristic of the chemical reaction.

The dilution factor characterizes the detection limit of the chemical reaction itself.

Typically, the dilution factor characteristic of the chemical reaction is attributed to dilution, concentration, or loss of material in preliminary stages of the chemical reaction. For example, a part of the reaction's reagents may be consumed in preliminary stages of heating, due to adherence to a reaction chamber's walls, etc.

Typically, the dilution factor is known in advance of the chemical reaction, say from previous runs of chemical reactions of the same type, in the same apparatus, general reference data available for the chemical reaction, etc., as known in the art.

That is to say that according to some exemplary embodiments of the present invention, there is allowed deviation of the calculated function's points from the calculated function's line of best fit, as long as the deviation is within an amplitude of change smaller than the signal amplitude attributed to the smallest detectable positive compound quantity, given the Measured Detection Limit associated by an instrument in which the reaction takes place, the reaction (method), and possibly, other requirements.

The Wikipedia web site defines the Limit of Detection (LOD), on a web page accessible through the URL: http://en.wikipedia.org/wiki/Detection_limit, as described in detail hereinbelow.

The measured detection limit is the maximum limit between the instrument detection limit (IDL) and the method detection limit (MDL).

In a setup that also quantifies the analyte, the detected limit will be the Limit of Quantification (LOQ)

Instrument Detection Limit is attributed to the noise and signal picked up by the device, given a blank sample is measured.

A blank sample is also referred to hereinabove, as a negative control sample (say a matrix without analytes)

The Instrument Detection Limit equals 3 times the standard deviation of the signal accepted when measuring the blank sample (Matrix without Analyte).

Method detection Limit is attributed to sample preparation, e.g. purifying the sample, digesting it, diluting it, using methods which introduce error into the system, etc.

The MDL may be estimated by multiplying the Instrument Detection Limit or Lower Level of Detection by the dilution prior to analyzing the sample solution on the instrument, or be measured more accurately by a statistical analysis of a set of samples near the expected limit of detection (LOD).

The Limit of Quantification is the limit at which we can reasonably tell the difference between two different values. It is estimated usually by multiplying the MDL by 5. It can be measured more accurately by statistical analysis of a set of samples near the MDL.

Hence, the limit of the amplitude (which may be denoted $A_m$) of the variations (i.e. deviations of the points of the calculated function points from calculated function's line of best fit), is the Standard Deviation of the blank sample measured by the device, times 3, times the dilution of samples during preparation, times 5:

$$A_m = 3 \cdot \text{std(noise)} \cdot \text{dilution} \cdot 5$$

Appendix-B

1. Given a function $y=F(x)$ where $x=0, 1 \ldots n$ and a sigmoid signal data $y=S(x)$ for the same x values 2. Our Shearing function is S-F will yield elbow points at min (S-F) and max (S-F):

3. We make a matrix of (n+1) by 2 where each row in this matrix contains x and f (x) then we compute the PCA (Primary Component Analysis) of this matrix. The result is two orthogonal vectors $V_1$ and $V_2$ and two scalar values, which are not consequential for this algorithm; the vector $V_1$ is the direction of the maximal variance of the points on the function F and can be used to plot a line-of-best-fit for F. of course, if F is already a straight line, than $V_2$ will be zero and $V_1$ will indicate the direction of the line F.

4. We define a line $y=L(x)$ which is a line in the 2D plain parameterized by the equation $V_1 \cdot t + B$ where $V_1$ is the vector resulting from step 3, t is the independent scalar parameter of the line, and B is a constant vector that determines where the line L cuts the axis of the plane.

The value of B is not important and in fact can be set to any vector; a reasonable value, for example, is the one resulting with minimal average error of this line from the function F, so as to have a best-fit line.

5. let $D(x)=L(x)-F(x)$ be the deviation (or error) of the straight line L from the function F; if F is a straight line, then D will be zero everywhere. Therefore, we can write S−F=S−L+D and thus D also gives us the deviation of using F for shearing the sigmoid signal S from using the straight line L for this shearing.

6. At this point, we place a necessary limitation on L and therefore also on F:

L must be parallel to another strait line that cuts the sigmoid in exactly 3 points. This cutting point can be within the measured (known) range, or outside this range. It is not necessary to know the exact cutting points, or to know the exact parallel line, but it is necessary that the line will be of that form. Otherwise the shearing will have no meaning for the goal of this analysis.

7. Let $S_1$ be the sheared version of the sigmoid, i.e. $S_1=S-L$, and let $S_f$ be the sheared version of the sigmoid using the function F i.e. $S_f=S-F=S_1+D$ (see step 5). Taking the minimal and maximal points of S1 as the elbow points of the sigmoid S is equivalent to the elbow points achieved by the linear function connecting the sigmoid two points, since L is parallel to a line that could have been chosen by the linear function. This is because any line that cuts the sigmoid in 3 points, could have been chosen, assuming that the reaction started in the first cutting point, and ended in the last cutting point. The equivalence between parallel lines is because the relative location of the maximal and minimal points on the sigmoid, remains the same, no matter which parallel line you choose.

8. Using the maximal and minimal points of $S_f$ as elbow points adds the factor D, which is in fact a noise factor, and so it would not be less accurate compared to $S_1$. If D is small enough at every point, then it could be possible to detect the elbow points even with $S_f$ without requiring the straight line $S_1$. In order to give some insight as to when the error factors in D are small enough we will describe an intuition of the effect they have on the results, but again, it would anyway be more accurate to use $S_1$ or, equivalently, the linear function connecting the two points of the sigmoid, as described in further detail hereinabove.

9. Let L' be a line parallel to L that cuts the sigmoid in exactly three points, which has the minimal error of L' from the Sigmoid S. Let $S_1'=S-L'$ be the sheared version of the sigmoid using L'. As we previously explained, using $S_1'$ for the analysis is equivalent to using $S_1$. Similarly, we can define $S_f'=S_1'+D$ and using it will be equivalent to using $S_f=S_1+D$.

Similarly to point 8, using $S_f'$ instead of $S_1'$ for the analysis adds an error factor D. Two different cases of error factor D, are described in the attached figures.

As long as the magnitude of the error D (which is determined by the shape of F) is significantly smaller than the magnitude of the elbow points in the sheared version of the sigmoid (the minimal and maximal points of $S_1'$), using $S_f'$ would be reasonably close to using $S_1'$ (Attached figure). However, if the magnitude of D is similar or greater to the magnitude of the elbow points (in the sheared version $S_1'$), then the addition of D (to create $S_f$) would distort the maximal and minimal points in such a manner that they would not be recognizable. The acceptable bounds of D are relative to the Signal Level attributed to the combined Limit Of Detection (LOD) of the analysis, and to the accepted tolerance to errors.

Since using straight lines, instead of other (nonlinear) functions, results with D being zero everywhere, such lines do not entail the described noise factors and would be anyway more accurate than using nonlinear function.

What is claimed is:

1. An apparatus for identifying transition points in a chemical reaction, the apparatus comprising:
    an electronic computing device comprising:
    a property value receiver, implemented on said electronic computing device, configured to receive a plurality of values of a physical property of the chemical reaction;
    a function calculator, associated with said property value receiver, configured to calculate a linear function parallel to and different from a linear function connecting two of the received values, the two values pertaining to a start and end of a time period;
    a difference calculator, associated with said function calculator, configured to calculate a difference between the calculated function and a plurality of the received values pertaining to the time period having said start and end;
    a transition point identifier, associated with said difference calculator, configured to identify at least one transition point of the chemical reaction, using the calculated difference; and
    a control operation initiator, associated with said transition point identifier, configured to initiate a control operation upon the transition point being identified.

2. The apparatus of claim 1, wherein the chemical reaction is a Polymerase Chain Reaction (PCR).

3. The apparatus of claim 1, wherein the values are photometric measurement values.

4. The apparatus of claim 1, wherein the values of the physical property start increasing substantially exponentially at the identified transition point.

5. The apparatus of claim 1, wherein the values of the physical property stop increasing substantially exponentially at the identified transition point.

6. The apparatus of claim 1, wherein the values of the physical property start decreasing substantially exponentially at the identified transition point.

7. The apparatus of claim 1, wherein the values of the physical property stop decreasing substantially exponentially at the identified transition point.

8. The apparatus of claim 1, further comprising a phase indicator, associated with said transition point identifier, configured to indicate a beginning of a phase of the chemical reaction upon the transition point being identified.

9. The apparatus of claim 1, further comprising a phase indicator, associated with said transition point identifier, configured to indicate an end of a phase of the chemical reaction upon the transition point being identified.

10. The apparatus of claim 1, further comprising a phase indicator, associated with said transition point identifier, configured to indicate an end of a preliminary stabilization phase of the chemical reaction upon the transition point being identified.

11. The apparatus of claim 1, further comprising a control operation initiator, associated with said transition point identifier, configured to initiate a control operation upon the transition point being identified.

12. The apparatus of claim 1, further comprising a monitoring data generator, associated with said transition point identifier, configured to generate monitoring data based on the identified transition point.

13. The apparatus of claim 1, further comprising a photometric measurement device, associated with said property value receiver, configured to measure the value of the physical property.

14. A computer implemented method for identifying transition points in a chemical reaction, the method comprising steps the computer is programmed to perform, the steps comprising:
    a) receiving a plurality of values of a physical property of the chemical reaction;
    b) calculating a linear function parallel to and different from a linear function connecting two of the received values, the two values pertaining to a start and end of a time period;
    c) calculating a difference between the calculated function and a plurality of the received values pertaining to the time period having said start and end;
    d) identifying at least one transition point of the chemical reaction, using the calculated difference, thereby proving for at least one of a group consisting of controlling the reaction, monitoring the reaction, and analyzing the reaction; and
    e) initiating a control operation of the chemical reaction upon said identifying of the transition point.

15. The method of claim 14, wherein the chemical reaction is a Polymerase Chain Reaction (PCR).

16. The method of claim 14, wherein the values are photometric measurement values.

17. The method of claim 14, wherein the values of the physical property start increasing substantially exponentially at the identified transition point.

18. The method of claim 14, wherein the values of the physical property stop increasing substantially exponentially at the identified transition point.

19. The method of claim 14, wherein the value of the physical property starts decreasing substantially exponentially at the identified transition point.

20. The method of claim 14, wherein the values of the physical property stop decreasing substantially exponentially at the identified transition point.

21. The method of claim 14, further comprising indicating a beginning of a phase of the chemical reaction upon said identifying of the transition point.

22. The method of claim 14, further comprising indicating an end of a phase of the chemical reaction upon said identifying of the transition point.

23. The method of claim 14, further comprising indicating an end of a preliminary stabilization phase of the chemical reaction upon said identifying of the transition point.

24. The method of claim 14, further comprising initiating a control operation of the chemical reaction upon said identifying of the transition point.

25. The method of claim 14, further comprising generating monitoring data based in the identified transition point.

26. The method of claim 14, further comprising measuring the value of the physical property.

* * * * *